United States Patent [19]

Atcher et al.

[11] Patent Number: 4,663,129

[45] Date of Patent: May 5, 1987

[54] ISOTOPIC GENERATOR FOR BISMUTH-212 AND LEAD-212 FROM RADIUM

[75] Inventors: Robert W. Atcher, Kensington, Md.; Arnold M. Friedman, Park Forest; John Hines, Glen Ellyn, both of Ill.

[73] Assignee: The United States of America as represented by the United States Department of Energy, Washington, D.C.

[21] Appl. No.: 696,547

[22] Filed: Jan. 30, 1985

[51] Int. Cl.[4] .......................... G21G 4/08; C01G 29/00; C22B 13/00; A61K 43/00

[52] U.S. Cl. .................................. 423/2; 250/432 PD; 252/645

[58] Field of Search ...................... 250/432 PD; 423/2; 252/645

[56] References Cited

U.S. PATENT DOCUMENTS 2,873,170 2/1959 Hyde et al. .............................. 423/2

4,206,358 6/1980 Matthews et al. ........... 250/432 PD

OTHER PUBLICATIONS

*Int. J. Nucl. Med. Biol.*, vol. 9, #1, p. 83, G. L. Zucchini et al., 1982.

Rosenow et al., "International Journal of Nuclear Medicine and Biology", vol. 10, pp. 189–197 (1983).

Buchanan et al., "International Atomic Energy Agency Conference at Copenhagen", vol. II, pp. 361–371 (1962).

Gansow et al., "ACS Symposium Series No. 241", pp. 216–227 (1984).

*Primary Examiner*—John F. Terapane

*Assistant Examiner*—Virginia B. Caress

*Attorney, Agent, or Firm*—James W. Weinberger; Arthur A. Churm; Judson R. Hightower

[57] ABSTRACT

A method and apparatus for providing radionuclides of bismuth-212 and lead-212. Thorium-228 and carrier solution starting material is input to a radiologically contained portion of an isotopic generator system, and radium-224 is separated from thorium-228 which is retained by a strongly basic anion exchange column. The separated radium-224 is transferred to an accessible, strongly acidic cationic exchange column. The cationic column retains the radium-224, and natural radioactive decay generates bismuth-212 and lead-212. The cationic exchange column can also be separated from the contained portion of the system and utilized without the extraordinary safety measures necessary in the contained portion. Furthermore, the cationic exchange column provides over a relatively long time period the short lived lead-212 and bismuth-212 radionuclides which are useful for a variety of medical therapies.

13 Claims, 4 Drawing Figures

ISOTOPIC GENERATOR FOR BISMUTH-212 AND LEAD-212 FROM RADIUM

CONTRACTUAL ORIGIN OF THE INVENTION

The U.S. Government has rights in this invention pursuant to contract No. W-31-109-ENG-38 between the United States Department of Energy and Argonne National Laboratory.

BACKGROUND OF THE INVENTION

This invention relates generally to an isotopic generator system as a source of bismuth-212 and lead-212 radionuclides. More particularly, the invention relates to an isotopic generator system which uses thorium-228 starting material in a radiologically contained portion of the system for producing radionuclides of bismuth-212 and lead-212 from an ion exchange column in an accessible generator portion of the system.

The practice of medical radiotherapy has previously involved the use of short lived α-emitting isotopes, such as $^{211}$At, and a β emitter, such as $^{131}$I (see, for example, Zucchini et al., "Isotopic Generator for $^{212}$Pb and $^{212}$Bi", International J. Nucl. Med. Biol. 9, 83 (1982); and Gansow et al., "Generator Produced Bi-212", American Chemical Society Symposium Series No. 214, January, 1984, which are incorporated by reference herein). In the case of cancer therapy, isotopes of lead-212 and bismuth-212 are combined in a chelated form with monoclonal antibodies which have a high specificity for cancer cells (see Zucchini and Gansow). However, in the case of $^{211}$At and $^{131}$I because both are halogens, there is a covalent reaction with tyrosine residues present in the antibody material, and there can be a consequent diminishment in activity and in the specificity for cancer cells. Furthermore, $^{131}$I delivers only low linear energy transfer $\beta^-$radiation which is not as effective as high linear energy transfer radiation, such as α-particles. Further, $^{131}$I emits γ rays which have the undesired effect of nonlocalized destruction of cells somewhat removed from the origin of the γ emIssIon. The $^{211}$At aIso must be produced by α-particle irradiation of bismuth in a cyclotron which limits the quantity of material produceable at a reasonable price. More recently, a chelated form of lead-212 has been used for immune suppression purposes, (see, M. K. Rosenow, "Properties of Liposomes Containing Pb-212", Intl. J. Nucl. Med. Biol. 10. 189–197, 1983). Further, a chelated form of bismuth-212 has been combined with monoclonal antibodies to provide a more stable radiotherapy agent with a high specificity for cancer cells. (see, p. 83 of Zucchini et al., cited hereinbefore). The bismuth-212 radionuclide is generated from decay of thorium-228 into radium-224 and radon-220 gas. The radon-220 gas is dissolved in water and separated from the thorium-228. Radon-220 has a half life of about one minute, and decay of the radon-220 leads to formation of lead-212 and consequent decay to bismuth-212. The short time for the decay of the radon-220 to form the desired lead-212 and its decay product, bismuth-212, makes it necessary to maintain the entire column as one unit. The long half life of 1.9 years for thorium-228 and the high level of radioactivity associated with the thorium-228, requires the use of a containment unit, such as a shielded facility or shielded glove box, for safe handling of the generator system. Furthermore, the ion exchange column used to retain the thorium-228 and the radium-224 undergoes substantial radiation damage degradation which requires periodic disassembly and reconstruction of the generator system. This particular prior art thorium-228 based generator system also necessitates periodic repurification of the thorium-228 source.

It is therefore an object of the invention to provide an improved method and apparatus for producing bismuth-212 and lead-212 radionuclides.

It is a further object of the invention to provide an improved generator system for producing bismuth-212 and lead-212 radionuclides from thorium-228 starting material.

It is another object of the invention to provide an improved radionuclide generator system having a radiologically contained portion with a plurality of valves for collection of radium-224 to enable formation and withdrawal of bismuth-212 and lead-212 from an ion exchange column in an accessible portion of the system which can be removed and utilized apart from the contained portion of the system.

It is an additional object of the invention to provide an improved radionuclide generator system which uses thorium-228 starting material disposed in a radiologically contained portion for producing radium-224 in an ion exchange column in an accessible generator portion which is removable from the contained portion and wherein a cation exchange media is used to retain the radium-224 to enable selective removal of bismuth-212 and lead-212.

SUMMARY OF THE INVENTION

In accordance with the present invention the radionuclide generator system utilizes thorium-228 starting material in a radiologically contained portion of the system to produce bismuth-212 and lead-212 radionuclides in a coupled, accessible generator portion of the system. A nitric acid carrier solution and thorium-228 is charged to the radiologically contained portion, and an anion exchange column is used to separate thorium-228 from radium-224. The thorium-228 remains on the anion exchange resin of the column, and the solution of nitric acid and radium-224 is transported to an evaporation unit wherein the acid solution is removed. A water solution of radium nitrate is formed and transferred from the evaporation unit to the accessible generator portion which is used for producing the bismuth-212 and lead-212 radionuclides. The accessible generator portion is a cation exchange column which retains the radium-224, and natural radioactive decay produces the desired bismuth-212 and lead-212 end products. In another aspect of the invention the radium nitrate solution can be output to the accessible generator portion by dispensing predetermined aliquots by a calibrated burette or pipette. In this manner a predetermined number of individual accessible generator portions can be dispensed and removed for end user application.

Further objects and advantages of the present invention, together with the organization and manner of operation thereof, will become apparent from the following detailed description of the invention when taken in conjunction with the accompanying drawings.

DETAILED DESCRIPTION OF THE PREFERRED EMBODIMENT

Figure 1:
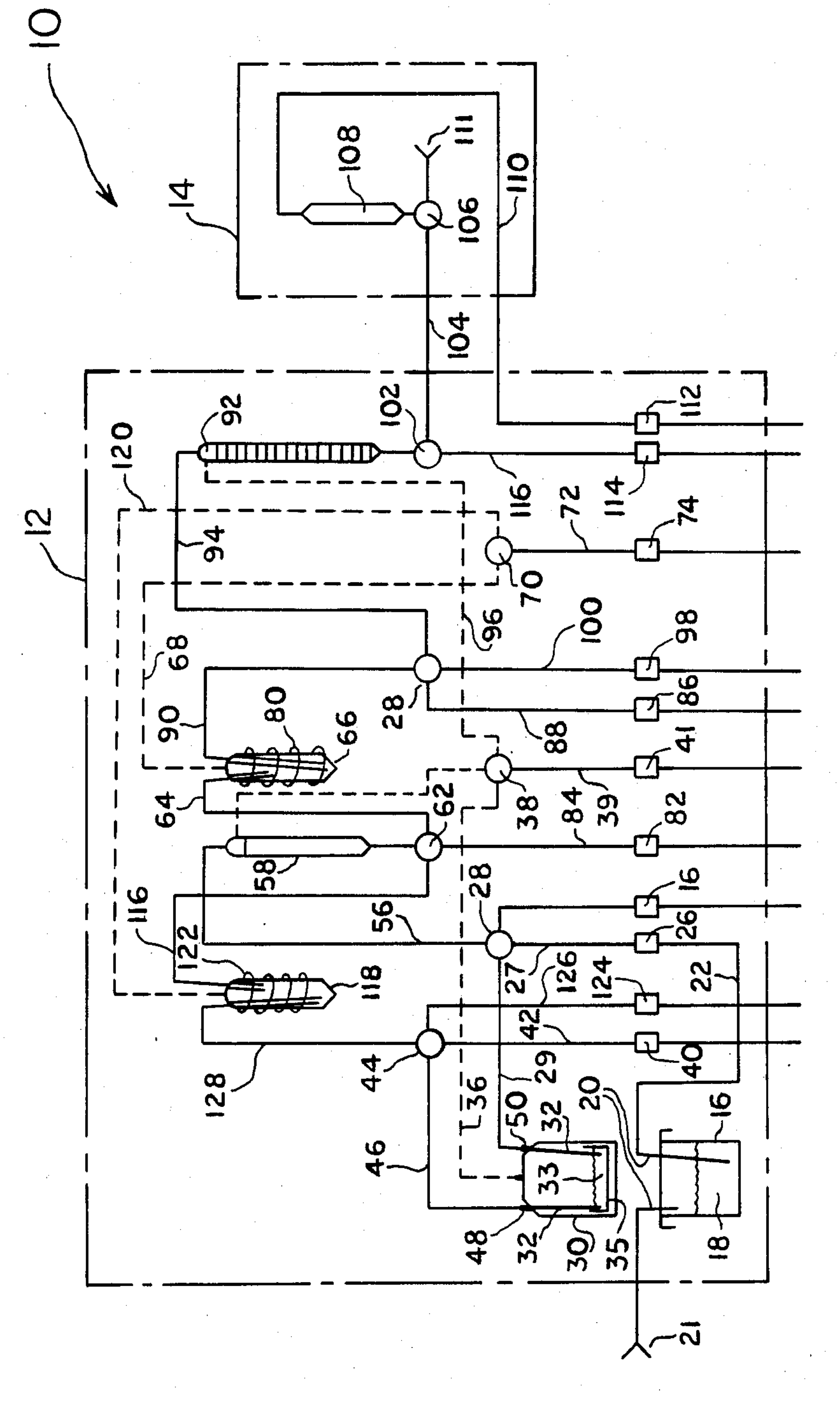
FIG. 1 illustrates a radionuclide generator system constructed in accordance with one embodiment of the invention.

Referring now to FIG. 1, one embodiment of the radionuclide generator system is indicated generally at 10. The generator system 10 is divisible into a radiologically contained portion 12 and an accessible generator portion 14. In general the production of the desired product radionuclides in the system 10 involves beginning the process with thorium-228 starting material in the contained portion 12, radium-224 is then separated from the thorium-228, the radium-224 is transferred to the accessible generator portion 14 and natural radioactive decay enables the production of bismuth-212 and lead-212 which is withdrawn for therapeutic medical use.

This division of the generator system 10 into the two portions 12 and 14 is preferable because highly active starting material, such as thorium-228, has a rather long half life (for example, 1.9 years for thorium-228) and the daughter materials exhibit high levels of $\gamma$ radioactivity. Consequently, these radioactivity characteristics require the use of expensive, inconvenient preparation facilities and of safety measures which are usually unavailable or impractical to implement for the end users of the product radionuclides. The system 10 has an advantage of allowing preparation of the desired radionuclides in the accessible generator portion 14 and shipment to the end user in a form which is safe for use without having to exercise extreme safety measures for long periods of time.

In the illustrated embodiment the contained portion 12 of the generator system 10 includes a supply means, such as a vial 16, which contains thorium-228 as a starting material 18 in the form of thorium nitrate complex in an eight molar solution of nitric acid as a carrier solution. There are also present in the solution equilibrium concentrations of nitrate ions of daughter materials, such as radium-224. The starting material 18 in the vial 16 is accessible by needle connections 20. New thorium-228 material is taken from the vial 16 whenever the recycled material from a previous production cycle is insufficient to produce the desired end product.

Flexible hose 22, such as ⅛ inch o.d. Teflon tubing, is coupled to the needle connections 20, and air pressure 21 is supplied from an external supply (not shown) to the starting material 18. The air pressure 21 forces the starting material 18 through the line 22 (in the illustrated embodiment the abovementioned ⅛ inch o.d. Teflon tubing is used for all line connections in the system 10). The starting material 18 then passes through a bulkhead fitting 26, along a line 27 and through a valve 28 positioned to deliver the starting material 18 through a line 29 to a supply container 30. The bulkhead fittings, such as the fitting 26, allow convenient, safe coupling to the Teflon tubing and ready access to the system components without having to disturb the connections intimately associated with the process components. Typically the various process components are mounted on a rigid sheet of aluminum or steel. In the illustrated embodiment, the bulkhead fitting 26 is a quick-disconnect, Luer taper plastic fitting (see, for example, the 1983–84 catalog of Rainan Instrument Co., Mack Road, Woburn, Mass. 01801, which is incorporated by reference herein). The valves 28 used throughout the system 10 are low pressure switching valves, such as a Hamilton Miniature HPV valve, (see, for example, p. 116 of the Rainan Instrument Company catalog described hereinbefore and incorporated by reference herein) having either three or four ports with single direction flow arrangeable between each of the pair of ports. The fittings to the valves 28 and the line 22 are preferably swivel connectors, such as H2461 detailed on page 103 of the Rainan catalog, described hereinbefore and incorporated by reference herein. In the illustrated embodiment these fittings are also used throughout the system 10.

Figure 3A:
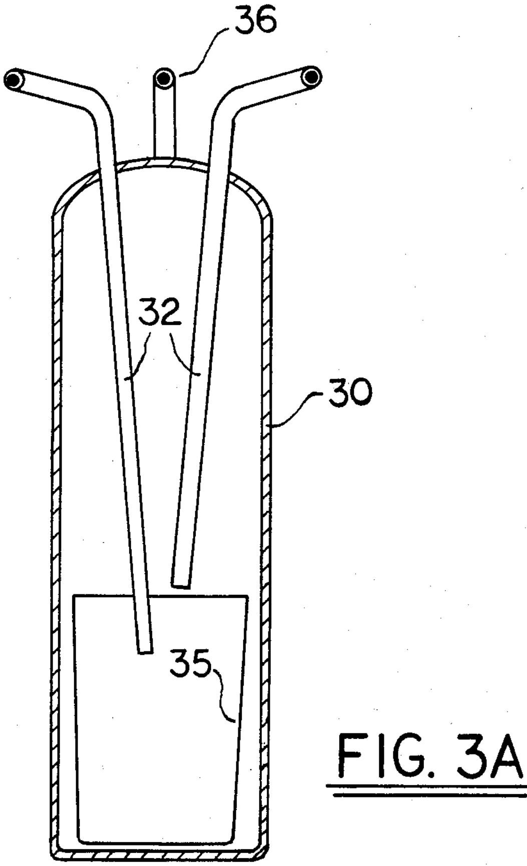
FIG. 3A is a side view and FIG. 3B is a top view of a sealed quartz container with quartz tubing providing access thereto.
Figure 3B:
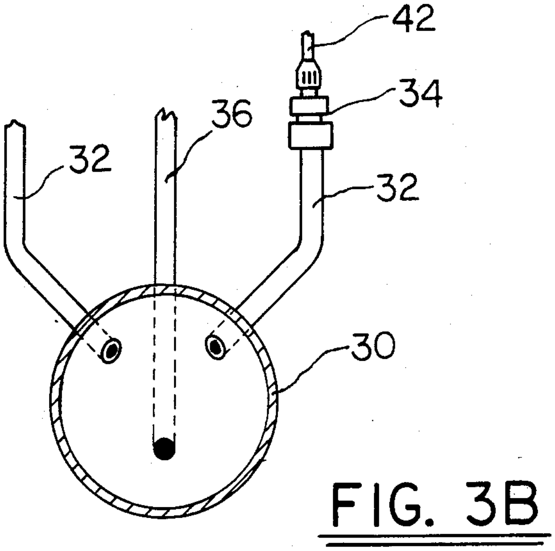

In FIG. 3 the supply container 30 is a sealed quartz vessel coupled from quartz tubing 32 to the flexible Teflon tubing by universal two way connectors 34 which are used throughout for all quartz to Teflon seals. Preferably the connectors 34 have a Tefzel type coupling for connecting to the flexible Teflon tubing, such as a line 36, and have a large bore end for coupling to the glass tubing 32 (see, for example, p. 109 of the Rainan catalog cited hereinbefore and incorporated by reference herein).

Referring to FIG. 1, in response to the air pressure 21, the starting material 18 from the vial 16 and/or any material recycled from a previous production cycle collects as supply material 33 in a platinum crucible 35 disposed within the supply container 30. Gas exhaust (substantially air and some radon) is output along the line 36, through a valve 38 and along a line 39 through a bulkhead fitting 41 to a gas trap or repository (not shown). Typically, a five gallon polyethylene bottle acts as a repository for both the gas and any waste material output from the various steps in preparing the radionuclides. The repository, or gas trap, allows the radon gas to decay to a nonvolatile species, such as lead-212 and bismuth-212. After accumulating the desired amount of the supply material 33 in the platinum crucible 35, air pressure is applied through another bulkhead fitting 40, through a line 42, a valve 44 and output along line 46 into a quartz tubing inlet 48. Responsive to the input air pressure the supply material 33 is transferred from the platinum crucible 35, through a quartz tubing outlet 50, along the line 29, through the valve 28 and along a line 56 into an anion exchange column 58. To equilibrate gas pressure and allow for fluid displacement, some exhaust gas (air and radon) is output from the column 58 along a line 60, through the valve 38 and along a line 39 through the bulkhead fitting 41 to the repository described hereinbefore. Preferably, the column 58 contains a strongly basic anion exchange media, such as, for example an AG 1, AG 2 or AG MP-1 exchange media having a chemical makeup of quaternary ammonium functional groups attached to a styrene divinylbenzene copolymer lattice (see pp. 7 and 8 of the January, 1984, catalog of Bio-Rad Chemical Division, 2200 Wright Avenue, Richmond, Calif. 94804, which is incorporated by reference herein). For purposes of this application the term exchange column is meant to include a container and its ion exchange media therein. The ion exchange media in the column 58 acts as separating means by retaining thorium-228, and allowing radium-224 and various daughter materials (see FIG. 2) to pass through in the nitric acid carrier solution. Documentation of the selectivity of strongly basic anion exchangers is set forth in FIG. 70 in Buchanan et al., *International Atomic Energy Agency, Copenhagen Conference on the Use of Radioisotopes in the*

*Physical Sciences and Industry,* Sept. 6–17, 1960, which is incorporated by reference herein.

In the illustrated embodiment the components of the system 10 are arranged to allow a gravity feed of the radium nitrate/nitric acid solution output from the exchange column 58, through a valve 62 and a line 64 to an evaporation unit 66. The gas exhaust from the unit 66 traverses a line 60, the valve 38, the line 39 and the bulkhead fitting 41 before terminating at the previously described repository (not shown). Similarly, the gas exhaust from the evaporation unit 66 is output through a line 68, a valve 70, a line 72 and through a bulkhead fitting 74 to the repository. The radium nitrate/nitric acid solution in the evaporation unit 66 has no detectable thorium-228 present. The exchange column 58 is then washed with about 10 milliliters of eight molar nitric solution to remove any residual radium-224. This nitric acid solution originates from an external source (not shown), and passes through a bulkhead fitting 76, a line 78, the valve 28, the line 56, the column 58, the valve 62 and the line 64 before emptying into the evaporation unit 66. The gas exhaust from the column 58 and the unit 66 follows the same paths as in the previously described step of gravity transfer from the exchange column 58 to the evaporation unit 66.

In order to prepare the radium-224 for generation of the bismuth-212 and lead-212 end products in the accessible portion 14, the nitric acid solution is removed from the evaporation unit 66 by evaporating the solution, leaving a dried compound of radium-224. In this embodiment the compound is radium-nitrate because $HNO_3$ was used to separate the thorium-228 from the radium-224 in the anion exchange column 58. A nichrome wire resistance heater 80 is wound around the evaporation unit 66, and approximately 50 to 80 watts of power are utilized to raise the temperature of the solution to increase the vapor pressure and evaporate all the water and concentrated nitric acid. Since the preferred solution is approximately an eight molar nitric acid solution, the water with a higher vapor pressure is driven off first, followed by sixteen molar concentrated nitric acid. In order to assist the elevated temperature evaporation process, air is input through a bulkhead fitting 82, passing through a line 84, the valve 62 and through the line 64 into the evaporation unit 66. The vapor exhaust from the evaporation unit 66 follows the gas exhaust path from the unit 66 discussed hereinbefore for the nitric acid wash step which removed residual radium-224 from the exchange column 58.

After the evaporation step has been completed, a liquid, such as water or 0.1M HCl, for dissolving the dried radium nitrate is input from an external source (not shown) to form a radium compound solution. The resulting radium-224 compound solution is transferred to the evaporation unit 66 through a bulkhead fitting 86, along a line 88, through the valve 28 and along a line 90 coupled to the unit 66. The water dissolves the dried radium nitrate, and exhaust gases from the unit 66 follow the same path discussed in the immediately previous paragraph. The radium nitrate solution is then ready for transfer from the evaporation unit 66 to a calibrated dispenser 92, such as a pipette or a burette. This dispenser 92 enables a predetermined number of aliquots to be output to the accessible generator portion 14, wherein the associated desired quantity of bismuth-212 and lead-212 can be produced. To carry out the dispensing operation, air is input to the unit 66 from the external air supply (not shown) via the fitting 82, through the line 84, the valve 62 and the line 64. Responsive to the air pressure the radium nitrate solution is output from the unit 66 along the line 90, through the valve 28 and the line 94 before input to the calibrated dispenser 92. The gas exhaust from the dispenser 92 passes through a line 96 through the valve 38, the line 39 and the fitting 41 to the repository described hereinbefore.

Each of the desired predetermined aliquots of radium nitrate solution is dispensed to the accessible portion 14 by a means for transferring, which includes various parts of the system 10, such as, for example, those elements of the system 10 defined by the following procedure: applying air pressure through a fitting 98, a line 100, the valve 28 and the line 94 coupled to the upstream side of the dispenser 92. The radium nitrate solution is output from the dispenser 92, through a coupled valve 102 and along a line 104 which joins the closed portion 12 with the accessible generator portion 14. The solution is then transferred through a valve 106 to retaining means, such as an ion exchange media, which retains the radium-224. The ion exchange media is held in container means, such as a cation exchange column 108. In the illustrated embodiment the predetermined aliquot of radium-224 cations undergoes ion exchange in the selected ion exchange media, such as, for example, a macroporous cation exchange AG MP-50 or another strongly acidic cation exchange media composed of, for example, sulfonic acid functional groups attached to a styrene divinylbenzene copolymer lattice (see, for example, pp. 7 and 8 of the January, 1984, catalog of Bio-Rad Chemical Division, cited hereinbefore and which is incorporated by reference herein). Effluent is output from the column 108 through a line 110 and a fitting 112 to the previously discussed repository.

Preparatory to removing the cation exchange column 108 from the system 10, various coupled supply lines must be decontaminated. Decontamination is effectuated by inputting air from an external source (not shown) via a fitting 114, along a line 116, through the valve 112, output through the line 104 and into the column 108 through the valve 106. The effluent from the column 108 passes through the line 110 and the fitting 112 to the repository for those radioactive species which are removed from the supply lines and are not retained by the column 108. As discussed hereinbefore, the repository functions generally as the waste container. The line 110 is then purged of radioactivity in preparation for removal of the column 108 by applying air pressure 111 to the valve 106, and the solution is output along the line 110 through the bulkhead fitting 112 to the repository.

Figure 2:
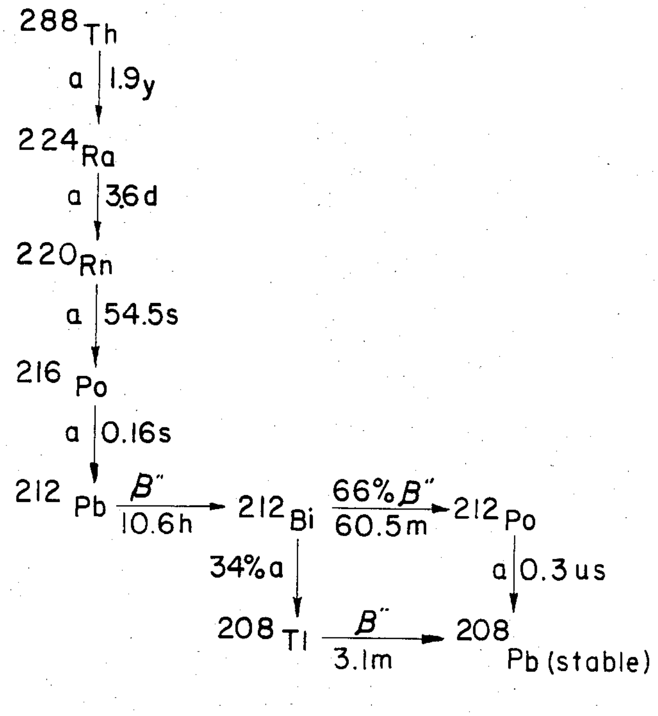
FIG. 2 depicts the $^{228}$Th decay series.

Once sufficient radium-224 is present in the cation exchange column 108 it can be disconnected and utilized as a completely separate isotopic generator system. In this case the radium-224 becomes a starting material provided by radium supply means, such as the contained portion 12. The user can collect selectively the end products of lead-212 and/or bismuth-212 radionuclides for medical applications such as, cancer treatment and suppression of immune response. Referring to FIG. 2, the radium-224 has a 3.6 day half life, and the desired end product radionuclide of lead-212 has approximately a 10.6 hour half life and the bismuth-212 has about a one hour half life. The 3.6 day half life of the radium-224 provides an adequate supply of lead-212 and bismuth-212 over a period of about two weeks time, and after about thirty-five to forty-five days the level of radiation is diminished sufficiently to enable disposal without extraordinary safety procedures.

Medical therapy applications, such as cancer treatment and immune response suppression, are particularly desirable applications for the lead-212 and bismuth-212 radionuclides because the bismuth-212 decays with emission of high energy α particles of various energies having an average of about 7.8 MeV energy. The sharp localization of radiation, high radiation density and high radiation level for each particle make bismuth-212 attractive for the above-mentioned medical treatments.

Selective withdrawal of the bismuth-212 and lead-212 radionuclides from the column 108 is accomplished by passing one or more acids of appropriate molarity through the cation exchange column 108. Useful acids include, for example, HCl, HI, HBr, $HNO_3$ and ascorbic acid. Each of these acids has appropriate ranges of molar concentration for selective removal of the bismuth-212 and/or lead-212.

In the case of HCl the bismuth-212 is first removed by a solution of lower appropriate molarity of about 0.25 to 1.0 and requires about one column volume (a standard known measure in the art of chromatography). If a molarity less than 0.25 is used, an increased number of column volumes is required. In order to remove lead-212, after withdrawal of bismuth-212, the exchange column 108 is charged with three column volumes of appropriate higher molarity HCl acid, about 1 to 6.

In the case of HI the bismuth-212 is first removed by a solution of appropriate molarity of about 0.05 to 0.20 HI for about one column volume. Subsequently, lead-212 is removed by using three column volumes of appropriate higher molarity of about 0.2 to 1.0 molar HI.

In the case of HBr the bismuth-212 can be removed by using about one column volume of appropriate molarity, or about 0.1 to 0.8 molar HBr. Subsequently, lead-212 is removed by using three column volumes of appropriate higher molarity of about 0.4 to 2.5.

In the case of $HNO_3$ the bismuth-212 can be removed by using about one column volume of appropriate molarity, or about 3 to 5 molar nitric acid, but $HNO_3$ alone cannot be used to remove lead-212.

Similarly, in the case of absorbic acid alone, lead-212 cannot be removed; however, about one column volume of appropriate molarity of about 1 to 2 molar absorbic acid removes most of the bismuth-212. Various combinations of these acids with appropriate molarity and column values can also be used to effectuate bismuth-212 and lead-212 removal from the exchange column 108.

After removal of the cation exchange column 108 for conveyance to the end user, a new one of the exchange columns 108 can be installed in the system 10, and the calibrated dispenser 92 can output to the column 108 another predetermined aliquot of the radium-224 nitrate solution. This procedure can be repeated by recycling a predetermined number of times until the predetermined aliquots are dispensed to each of the exchange columns 108.

Referring again to FIG. 1, after dispensing of the radium-224 solution by the calibrated dispenser 92, the contained portion 12 can undergo a recycling operation to prepare a completely new batch of the radium-224. This is accomplished by chemically stripping the thorium-228 from the anion exchange column 58. Water and then six molar hydrochloric acid is input to the column 58 through the fitting 76, along the line 78, through the valve 28, along the line 56 into the column 58, thereby washing the nitric acid from the column 58 through the valve 62 and through a line 116 into a thorium evaporation unit 118. Responsive to the input of water, HCl and residual $HNO_3$, exhaust gas is output from the evaporation unit 118 along a line 120, through the valve 70, along the line 72 and through the fitting 74 to the previously described repository. Gas exhaust is also output from the ion exchange column 58 along the line 60, through the valve 38, and output along the line 39 and through the fitting 41 to the repository.

To carry out evaporation of the solution in the evaporation unit 118, about 50 to 80 watts of heat are applied by a nichrome wire heater 122. In order to assist the elevated temperature evaporation process, air is input through the fitting 82, the line 84, through the valve 62 and output along the line 116 into the unit 118. Elevated temperature evaporation proceeds in the order of water, hydrochloric acid and nitric acid with vapors of these chemical compounds output along the line 120, through the valve 70, the line 72 and output through the fitting 74 to the repository. Upon completion of the evaporation process, residual thorium-228 material remains in the unit 118. This residual thorium-228 is dissolved in additional eight molar nitric acid which is transferred into the evaporation unit 118 through a fitting 124, a line 126, the valve 44 and output through the line 128 into the unit 118. Exhaust air and radon gas are output along the same path as the evaporated water and acids described at the beginning of this paragraph.

In the final step of the illustrated embodiment, the thorium-228, nitric acid solution is returned to the supply material 33 in the platinum crucible 35 disposed within the supply container 30. This step is accomplished by applying air pressure to the evaporation unit 118. Air from the external source (not shown) is input through the fitting 82, the line 84, the valve 62, and output through the line 116 into the unit 118. The thorium-228, nitric acid solution is output along the line 128, through the valve 44 and the line 46 into the platinum crucible 35 wherein the supply material 33 is contained. Air and radon are output from the supply container 30 along the line 36, through the valve 38 and output through the line 39, through the fitting 41 to the repository described hereinbefore. Once the thorium-228 has been returned to the platinum crucible 35, the system 10 is ready to operate again provided a sufficient quantity of radium-224 has been generated in the supply material 33. This procedure helps to minimize radiation damage to the anion column 58 and the various quartz containers, such as the thorium evaporation unit 118.

The present invention provides improved methods and apparati which use thorium-228 supply material disposed in a radiologically contained portion for producing bismuth-212 and lead-212. The bismuth-212 and lead-212 are generated in an accessible generator portion which can be removed and safely utilized apart from the radiologically contained portion 12 which encloses the relatively hazardous part of the generator system 10. Radium-224 is retained on a cation exchange column of the accessible generator portion 14, and the relatively long (3.6 day) half life of radium-224 provides a long term beneficial output of the short half life lead-212 and bismuth-212, about ten hours and one hour half life, respectively.

The following example is included for illustrative purposes only and is not intended to limit the scope of the invention.

EXAMPLE

The generator system is located in a $\gamma$ shielded facility (a cave) in the Chemistry Division of Argonne National Laboratory, Argonne, Ill. Shielding is required because some of the short lived daughter activities include high energy $\gamma$ radiation, as well as $\alpha$ and $\beta$ radiation. The cave is at a negative pressure relative to atmospheric pressure for control of potentially hazardous gas emission. Manipulation of valves and changing of ion exchange columns is done by master slave manipulators. All exhaust of air and liquids is through tubing which terminates in a five gallon polyethylene container. This radiologically controlled generator system permits entrapped radon with a half life of about one minute to decay to a nonvolatile species, such as lead-212 or bismuth-212. The apparatus remains free of external contamination to facilitate any emergency repairs. Reagent solutions and air for liquid transfer and drying purposes are supplied from outside the cave through the cave walls by means of 1/16 inch i.d. silicone rubber tubing. Reagents are measured and dispensed through these tubes by glass hypodermic syringes. Air flow is controlled by a commercial pressure regulator and an adjustable flowmeter.

The apparatus for generation of bismuth-212 and lead-212 is constructed primarily of quartz and Teflon for maximum resistance to chemical and radiological damage. Only those parts which are not subject to such conditions (air lines and reagent water lines) are made of less resistant silicone rubber. Disposable items which need only survive one cycle also are constructed of less resistant material. Except for the platinum crucible which holds the thorium-228 supply material, the rest of apparatus is in intimate contact with the acids and thorium-228 material for less than three hours in a two week cycle.

All acid solutions are prepared from chemically pure reagent grade acids diluted with deionized and distilled water. The ion-exchange resins used are from a commercial supplier, Bio-Rad Chemical Division, Richmond, Calif. One of the preferable anion resins, Dowex-1, is supplied in a chloride form and must be converted to the nitrate form by repeated alternate washing with 6 molar $HNO_3$ and water. The cation resin, such as AG MP50, 100–200 mesh, must be conditioned by alternate acid/water washes to insure the resin is in the hydrogen form and free of extraneous cations. The resins are treated in a relatively large batch to insure an ample supply of uniform quality and are stored in water until needed.

A cycle or production batch run begins by packing a Bio-Rad Econo disposable ion exchange column with $\frac{3}{4}$ milliliter of conditioned anion resin. A glass wool plug is inserted on top of the resin bed to minimize disruption of the bed by subsequent operations. The resin is preconditioned with 5 milliliters of 8 molar $HNO_3$. The cation exchange column is filled with 0.4 milliliters of cation resin, and water is used to condition this column. The anion column is mounted in the separation apparatus by inserting the male Luer connection on the discharge end of the column into the mating fitting on the top of the coupled valve. The input end of the column is similarly coupled into the system with Luer fittings.

A 5 milliliter charge of 8 molar $HNO_3$ is injected into the thorium-228 supply container using an external hypodermic syringe. The nitric acid carrier solution dissolves the thorium-228 and daughter material (such as radium-224) nitrates and complexes the nitrates for adsorption on the anion resin. About 5 psi of air pressure is used to move the nitrate solution to the anion column. The solution moves through the anion resin bed into the radium evaporation unit under the force of gravity. Thorium-228 is adsorbed on the anion resin and radium-224 passes into the evaporation unit. To insure complete recovery of the radium-224, an additional 10 milliliters of 8 molar $HNO_3$ acid is washed through the resin using an external syringe. The combined 15 milliliters of nitric acid containing the radium-224 and daughter activities is evaporated using a nichrome wire-wound electric resistance heater at 50–80 watts of power. To speed the evaporation process, air at 5 psi and 0.2 liters/minutes is passed through the evaporation unit which is heated to dryness. Five milliliters of water is injected into the evaporation unit to dissolve the radium-224 nitrate. Five psi of air pressure transports the radium-224 nitrate solution from the evaporation unit into the calibrated dispenser. The dispenser is used to aliquot the requisite predetermined quantity of radium-224 to the cation exchange column in which is generated the radionuclides of bismuth-212 and lead-212. This is accomplished by applying 0.1 psi of air pressure to the dispenser transferring the solution to the cation exchange column. After an air purge of the cation exchange column and its associated tubing, the cation exchange column is manually disconnected from the closed portion of the system, and its mating Luer fittings at each end are secured together to minimize radon leakage. It is then inserted into a shielded shipping pot for distribution to the user. The next cation exchange column is mounted and the cycle of dispensing radium-224 is repeated for the desired predetermined number of times. The operational range of the above-described accessible portion 14 is capable of providing output radionuclide quantities in the range of twenty to fifty millicuries for each batch, and the apparatus can be enlarged to provide greater quantities if desirable.

The thorium-228 adsorbed on the anion exchange column should also be desorbed and returned to the supply container to minimize radiation damage effects and to recycle material to begin production again. This process can be carried out concurrently with the loading of the cation exchange column described above. A 10 milliliter water wash will remove about 85–90% of the thorium-228 from the cation exchange column. An additional 10 milliliter wash of 6 molar HCl will desorb most of the remainder. The washings flow by gravity into the thorium-228 evaporation unit, and the thorium-228 solution is evaporated to dryness in the same manner as the radium-224 solution. The dried salt of thorium-228 is dissolved in 5 milliliters of 8 molar $HNO_3$, and five psi of air pressure moves the thorium-228 solution back to the supply container. The used anion exchange column is normally discarded, and before commencing the next production cycle the system is left in an "idle" state to replenish the radium-224 removed in the production process. In this idle condition the radiation heating of the thorium-228 and daughter material in the supply container will evaporate the $HNO_3$ solution.

Although the present invention is described in terms of specific process steps, components and materials, it will be clear that various modifications within the skill of the art may be made within the scope of the following claims. Various features of the invention are set forth in the following claims.

The embodiments of this invention in which an exclusive property or privilege is claimed are defined as follows:

1. In an isotopic generator system, a method of using thorium-228 supply material disposed in a raiologically controlled portion of the system for producing radionuclides of bismuth-212 and lead-212 in a cation exchange resin bed, comprising the steps of:

(a) separating radium-224 from a solution of thorium-228 supply material in an approximately 8 molar nitric acid in said radiologically contained portion by passing said solution through a strongly basic anion exchange resin;

(b) transferring said radium-224 to said cation exchange resin bed from said radiologically contained portion;

(c) producing said bismuth-212 and lead-212 radionuclides by decay of the Radium-224 in said cation-exchange resin bed; and (d) eluting said bismuth-212 and lead-212 from said cation exchange resin bed with acid.

2. The method as defined in claim 1 further including the step of selectively withdrawing from the cation exchange resin bed portion at least one radionuclide selected from the group consisting of bismuth-212 and lead-212.

3. The method as defined in claim 1 wherein said step of separating radium-224 comprises:

passing said solution through said anion exchange resin and providing an output from said exchange column;

filling an evaporation unit with said output from said exchange column;

producing a dried compound of said radium-224 by evaporating in said evaporation unit said output from said exchange column; and charging a liquid into said evaporation unit to dissolve said radium-224 compound.

4. The method as defined in claim 3 wherein said liquid is a member selected from the group consisting of water and 0.1 molar HCl.

5. The method as defined in claim 3 wherein said anion exchange resin comprises quaternary ammonium functional groups attached to a styrene divinyl benzene copolymer lattice.

6. The method as defined in claim 3 wherein said thorium-228 supply material comprises a 8M nitric acid solution of thorium-228 and daughter materials and said radium-224 compound comprises radium-224 nitrate.

7. The method as defined in claim 2 wherein said step of selectively withdrawing bismuth-212 comprises inputting to said cation exchange resin bed a first acid selected from the group consisting of hydrochloric, hydroiodic, hydrobromic, nitric and ascorbic acid.

8. The method as defined in claim 7 wherein said step of selectively withdrawing comprises preferentially removing said bismuth-212 and subsequently inputting to said cation exchange resin bed a second acid to remove preferentially said lead-212, said second acid selected from the group consisting of hydrochloric, hydroiodic and hydrobromic acid, and having a higher molarity than said first acid.

9. The method as defined in claim 8 wherein said first acid comprises hydrochloric acid with a molarity from about 0.25 to 1.0 and said second acid comprises hydrochloric acid with a molarity from about 1 to 6.

10. The method as defined in claim 8 wherein said first acid comprises hydroiodic acid with a molarity from about 0.05 to 0.20 and said second acid comprises hydroiodic acid with a molarity from about 0.02 to 1.0.

11. The method as defined in claim 7 wherein said first acid comprises nitric acid with a molarity from about 3 to 5.

12. The method as defined in claim 7 wherein said first acid comprises ascorbic acid with a molarity from about 1 to 2.

13. An isotopic generator system for providing bismuth-212 and lead-212 radionuclides for selective removal and therapeutic medical use, comprising:

radium supply means for providing radium-224 starting material, said radium supply means comprising thorium-228 supply material;

means for separating radium-224 from a solution of thorium-228 supply material in an approximately 8 Molar nitric acid in a radiologically contained portion of said system by passage of said solution through a strougly basic anion exchange resin;

means for transferring said radium-224 to a cation exchange resin bed from said radiologically contained portion;

means for producing said bismuth-212 and lead-212 radionuclides in said cation exchange resin bed; and eluting said bismuth-212 and lead-212 from said cation exchange resin bed with acid.

* * * * *